United States Patent
Haney

(10) Patent No.: US 9,417,162 B2
(45) Date of Patent: Aug. 16, 2016

(54) GAS TRAP EXPANSION CHAMBER

(71) Applicant: Perry Haney, Tahoka, TX (US)

(72) Inventor: Perry Haney, Tahoka, TX (US)

( * ) Notice: Subject to any disclaimer, the term of this patent is extended or adjusted under 35 U.S.C. 154(b) by 365 days.

(21) Appl. No.: 14/220,143

(22) Filed: Mar. 20, 2014

(65) Prior Publication Data
US 2015/0267488 A1    Sep. 24, 2015

(51) Int. Cl.
| | | |
|---|---|---|
| *G01N 33/18* | (2006.01) | |
| *G01N 1/22* | (2006.01) | |
| *G01N 1/00* | (2006.01) | |
| *G01N 1/20* | (2006.01) | |
| *E21B 21/06* | (2006.01) | |
| *E21B 21/01* | (2006.01) | |

(52) U.S. Cl.
CPC ......... *G01N 1/22* (2013.01); *E21B 21/01* (2013.01); *E21B 21/067* (2013.01)

(58) Field of Classification Search
CPC ..... E21B 49/086; E21B 21/01; E21B 21/067; G01N 33/2823; G01N 2001/2267; G01N 1/2247; G01N 2001/1025; G01N 33/18; G01N 1/22; G01N 1/20; G01N 29/02; G01N 2291/022; G01N 2291/0222; G01N 2291/0228; G01N 2291/02433; G01N 33/1806; G01N 33/0011; G01N 2001/4016; G01N 33/2841; B05D 3/144; B23K 35/262; B23K 35/3033; B32B 2260/04; B32B 2307/206; B32B 2307/304; B32B 2457/04; B32B 27/281; B32B 27/34; B32B 7/08; B32B 7/12; B32B 7/14; B32B 9/00; C22C 13/02
USPC .............. 73/19.12, 19.1, 863.51, 863.81; 175/206; 95/282
See application file for complete search history.

(56) References Cited

U.S. PATENT DOCUMENTS

| | | | | |
|---|---|---|---|---|
| 5,036,697 A | * | 8/1991 | Fujiwara ............ | B01D 19/0042 62/126 |
| 5,199,509 A | * | 4/1993 | Wright ............... | B01D 19/0052 175/206 |
| 8,584,518 B2 | * | 11/2013 | Phillips .............. | B01D 19/0052 73/152.04 |

* cited by examiner

*Primary Examiner* — Lisa Caputo
*Assistant Examiner* — Brandi Hopkins
(74) *Attorney, Agent, or Firm* — Norred Law, PLLC; Warren V. Norred

(57) ABSTRACT

The invention allows for the collection of formation gases by placement of an agitating pipe directly in the drilling fluid flow line; the pipe's opening cut at an angle so gas in the top half of the drilling fluid flow line will be collected and also analyzed, along with the gas agitated from the drilling fluid. An expansion chamber is disclosed which encourages the drilling fluid flow line to release the gas held within it, so sample testing of the gases is more accurate than it would be in the prior art.

6 Claims, 4 Drawing Sheets

51

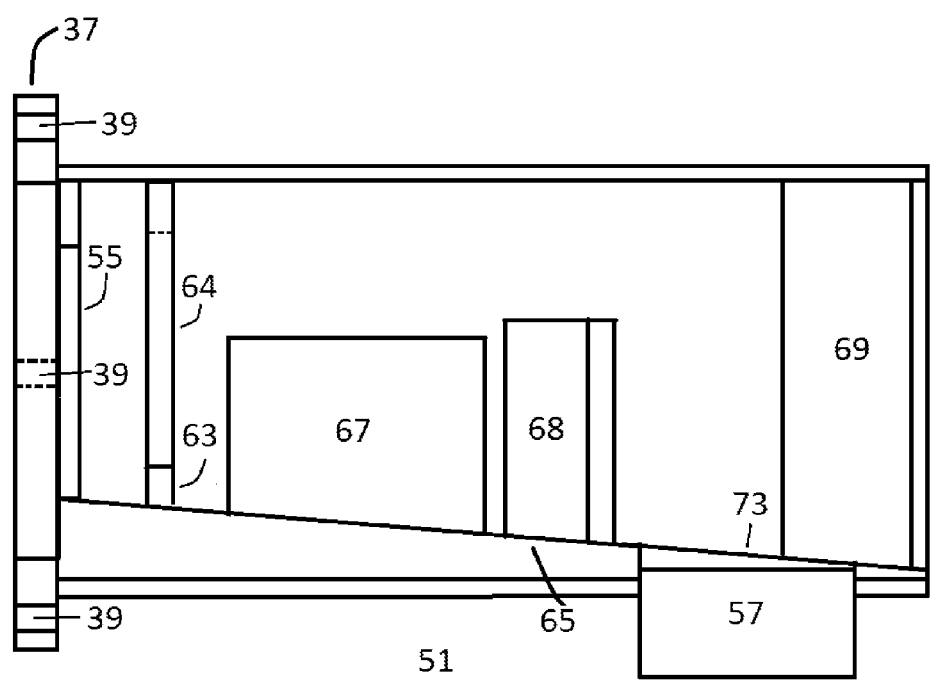

GAS TRAP EXPANSION CHAMBER

A. THIS APPLICATION IS A CONTINUATION IN PART OF U.S. SER. NO. 13/337,035

Figure 1:
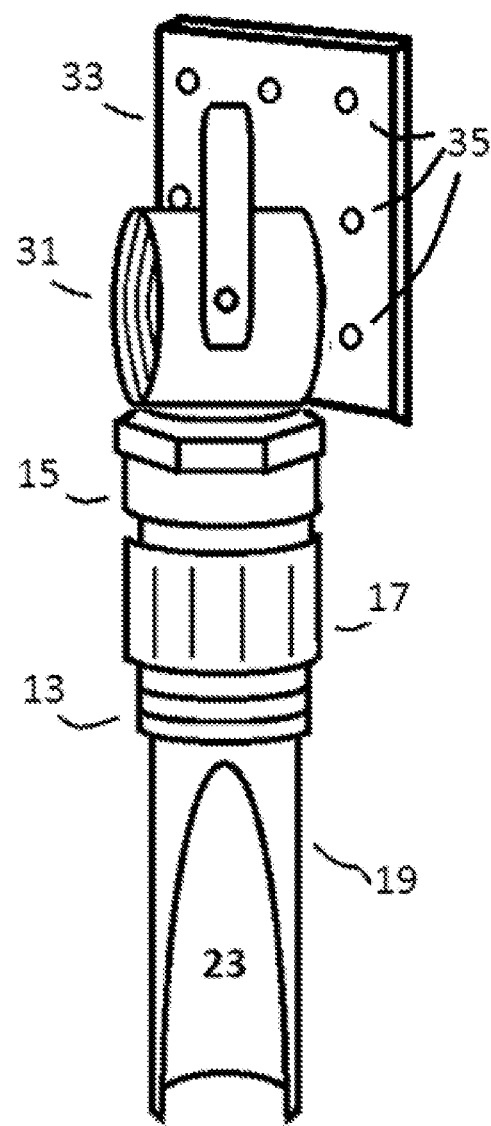

This application is a continuation-in-part application depending upon Ser. No. 13/337,035, which was allowed by the USPTO on Jan. 17, 2013, but is pending at the time of this filing, share the same inventor, and which is incorporated by reference in full.

B. TECHNICAL FIELD OF THE INVENTION

The invention pertains to the collection of formation gases as oil wells are drilled, specifically a chamber that encourages the release of such gases from processing fluids.

C. BACKGROUND OF THE INVENTION

The oil and gas industry has always treated the collection of formation gas and formation cuttings data as one function. On an oil and gas drilling project, there are two different applications. The first drilling application is the collection of formation gases and cuttings while the drilling fluid is directed to the reserve pits. The second drilling application is the collection of formation gases and cuttings while the drilling mud is directed to the steel pits.

The traditional configuration begins at the well head. From the well head, there is a flow line in which the drilling fluid leaves the well bore. The flow line is commonly 160 mm or 225 mm (six or eight inches) in diameter. The flow line extends from the well head out towards the steel and reserve pits, where there are control valves that control the direction of the drilling fluid, either to the reserve pits, or to the steel pits. The reserve pits are located further away from the well bore and behind the steel pits. The drilling fluid from the well head carries the formation gases and formation cuttings from the well bore, to either the reserve pits, or the steel pits. The formation cuttings are dumped into the reserve pits, where they cannot reenter the drilling system. The formation gases are either released into the atmosphere, or flared off. The drilling fluid is then circulated around into the well bore, where the process is restarted.

Drilling Phase One—Water/Reserve Pits—At the beginning of a drilling project, the 30 drilling fluid is either fresh water or brine water. The drilling fluid is bypassed the steel pits and out to the reserve pits, which are located behind the steel pits. The reserve pits are earth dug pits, in the shape of a horseshoe and at a slight angle. This allows the formation cuttings to be dropped out of the fluid. The fluid flows around to the other end of the horseshoe where it is suctioned back into the well bore. The flow line is an open ended system, so there is no any pressure on the flow line. The flow line is filled approximately halfway with drilling halfway with drilling fluid. The drilling fluid is a mixture of formation gases and formation cuttings. The top half of the flow line is filled with formation gases.

Current practice in the industry is to insert a two-inch line into the flow of drilling mud, diverting it to the formation cuttings sample box that is installed near the end of the drilling fluid flow line and installed low enough, relative to the drilling mud source, so the fluid flows easily into the formation sample box.

The formation cutting sample box is a rectangular box, with a sliding door in the front.

The formation cutting sample box is designed for catching formation cuttings, as well as holding enough drilling fluid for the agitator, for monitoring formation gas. Its width and length must be wide enough, to allow a sample box agitator stand to fit inside, and long enough, as not to hinder the collection of formation cuttings to be analyzed. It must also be built sturdy enough to withstand the vibration from the agitating motor, as well as the combined weight of the agitating stand and motor. The sliding door has a handle cut along its top edge. The handle is to allow excess fluid to flow out of the sample box, out into the reserve pits and not over the sides or end of the sample box. The sliding door is also used for washing formation cuttings out into the reserve pits, after a sample is collected, so that the next ten foot sample can be caught inside the sample box.

The sample box agitating stand is a steel stand about three to four feet tall, onto which the agitator motor is mounted. The stand has an entrance and exit portal in it that allows drilling fluid to enter and leave the box. An explosion-proof electrical agitator motor is mounted on the box which rotates beaters affixed to the motor's rotating shaft. A suction hole is drilled in the sample box to allow formation gases to be sucked out of the sample box to be analyzed.

Drilling Phase Two—Mudding Up/Steel Pits—At some point in the drilling process, the crews will begin to "mud up", a term used by the oil and gas industry to describe the process of adding chemicals to the drilling fluid to control the properties of the drilling mud. At this point, the drilling fluid is now referred to as drilling mud. Once the determination has been made to start mudding up, the two valves are turned in the drilling fluid flow line and the flow is diverted from the reserve pits to the steel pits. Then chemicals are mixed to start the mudding up process. The drilling mud is directed to the steel pits to: 1) begin the mudding up process, 2) prevent loss of expensive drilling mud, 3) to maintain, control, and change the properties of the drilling mud, 4) to protect the well bore, and 5) to prevent or control lost circulation.

During the second phase, when drilling mud is used, the agitator stand is placed inside the sample box, at a lower bottom of a large vat, known as the possum belly, located in front of the shaker. The drilling fluid flow line enters into the possum belly at its base. The drilling mud fills the possum belly, until the drilling mud spills over the front edge, onto the shaker. The shaker includes screens and vibrates very rapidly. The drilling mud and formation cuttings spill onto the screens. The vibration of the shaker allows the drilling mud to fall through the screens, into the steel pits, leaving the formation cuttings on the screens. The drilling mud is remixed and suctioned back into the well bore. The formation cuttings are vibrated to the end of the shaker where they fall onto a slide. A sample of the formation cuttings is collected off the slide for examination. Formation gases are collected for monitoring at the possum belly. The remainder is washed off the slide, into the reserve pits.

The traditional method beats gases trapped out of the drilling fluid that is collected in the sample box, and only those gases. The sample box has to be moved when the drilling starts the mudding up process. The gas in the top half of the drilling fluid flow line simply escapes into the atmosphere and is never analyzed. Formation cuttings fill the formation cuttings sample box, plugging the hole at the base of the agitator bracket, and cause improper formation gas readings. The end result is that formation gases either cannot be monitored at all, or have very inaccurate readings. The traditional method also uses an agitating motor that vibrates, rusts, and requires electrical power in an outdoor installation. In such an environment, loss of power or a rusted motor renders the sampling system unusable.

The oil industry needs to be able to more efficiently sample the gases coming up out of the well with the drilling fluid.

D. SUMMARY OF THE INVENTION

The invention allows for the collection of formation gases by placement of an agitating pipe directly in the drilling fluid flow line; the pipe's opening cut at an angle so gas in the top half of the drilling fluid flow line will be collected and also analyzed, along with the gas agitated from the drilling fluid. Because of the design of the gas trap of the invention, formation cuttings will not plug up the gas trap, but flow around the agitator pipe and out to the sample box.

This continuation-in-part application depends upon Ser. No. 13/337,035; the new material discloses a Gas Trap Expansion Chamber which is added to the construction of the invention of U.S. Ser. No. 13/337,035. This Expansion Chamber adds further agitation of the drilling fluid as it is travels through the Chamber and is discharged through the Expansion Chamber's drain.

E. BRIEF DESCRIPTION OF THE SEVERAL VIEWS OF THE DRAWING(S)

Exemplary embodiments of the gas trap are set forth in the figures below.

FIG. 1—Orthogonal view of the Agitating Pipe, Ball Valve, and Mounting Plate.

Figure 2:
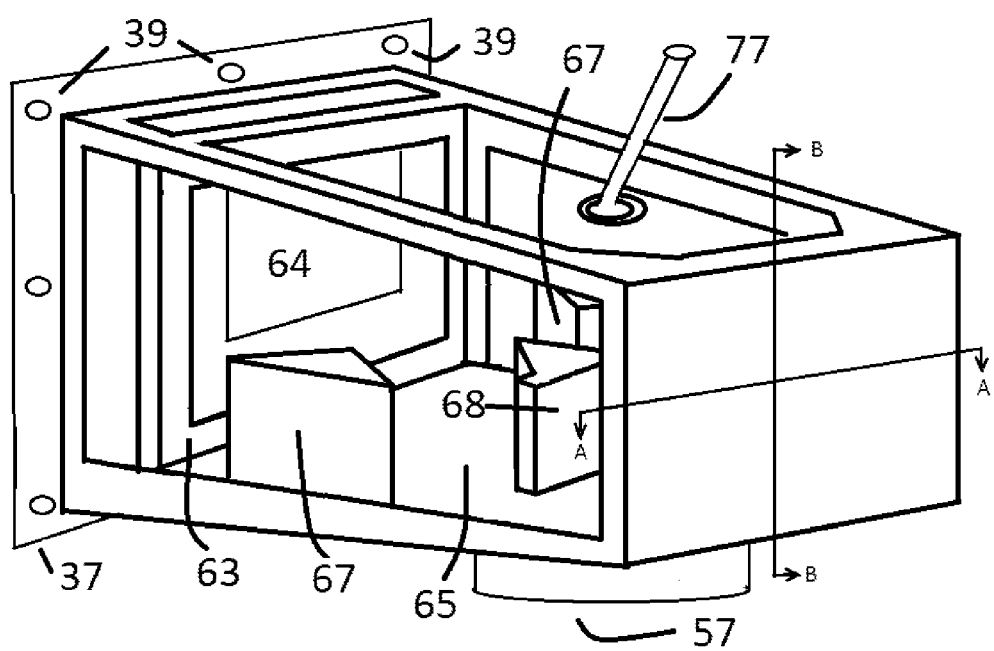

FIG. 2—Orthogonal view of the Expansion Chamber.

Figure 3:
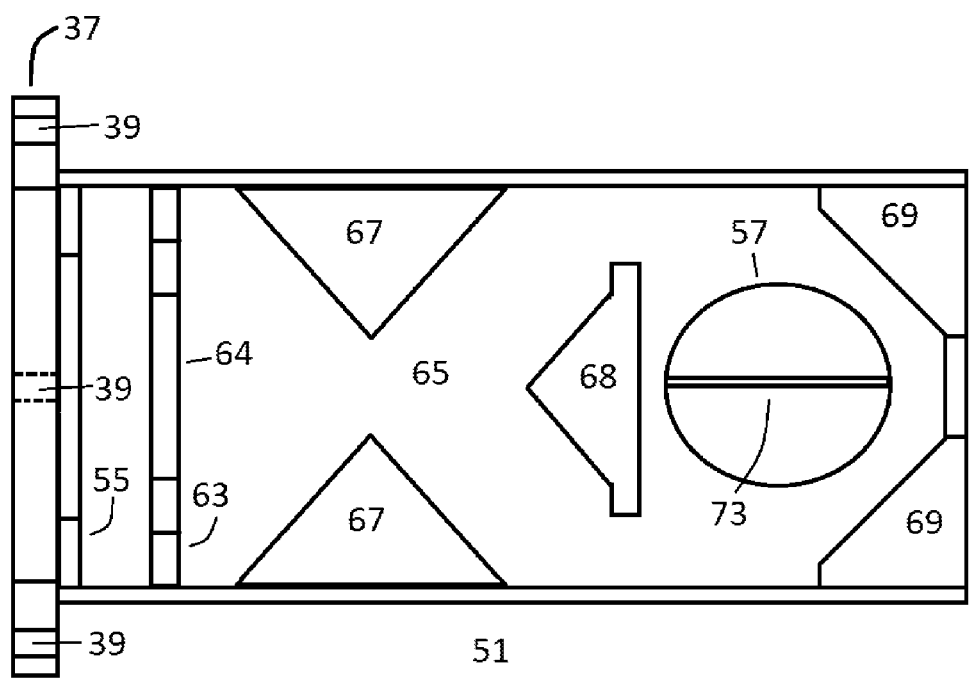

FIG. 3—Cross-sectional Top View of the Expansion Chamber.

FIG. 4—Cross-sectional Side View of the Expansion Chamber.

F. BRIEF DESCRIPTION OF THE DRAWINGS

For a better understanding of the disclosure, and to show by way of example how the same may be carried into effect, reference is now made to the detailed description along with the accompanying figures in which corresponding numerals in the different figures refer to corresponding parts.

G. DETAILED DESCRIPTION OF THE INVENTION

As a reminder, this application is a continuation-in-part application depending upon Ser. No. 13/337,035, which is incorporated in full herein. This application focuses on the Expansion Chamber 51, which is added to construction to further assist in gas separation from the flow liquid, making the sampling process more efficient, reliable, and accurate.

As shown in the figures, a user employs a Valve 31 which allows sample fluid to flow up through the Agitating Pipe 23, through the Valve 31, the Valve-Side Mounting Plate 33, the Chamber-Side Mounting Plate 35, through the Entrance Portal 55 and into the Expansion Chamber 51 on the side of one end, and leaves through the Drain 57 on the bottom of the side farthest from the Entrance Portal 55.

Though the current embodiment employs a Valve 31, the Valve 31 is optional. The Agitating Pipe 23 may be connected directly to the Expansion Chamber 51; the Valve 31 assists to control the flow when it exceeds a preferred rate.

The Valve 31 may be a simple two-way valve that prevents excessive flow or shuts off the sample fluid through the pipe completely, or it may be a three-way (or more) valve that discharges the flow from the Agitating Pipe 23 through the Chamber 51, or to optional drain paths.

As shown in FIGS. 2 and 3, the Expansion Chamber 51 employs a number of agitating elements to force the sample fluid to agitate the fluid further, releasing gas stored in the liquid. These elements include:

a) an Entrance Constrictor Frame 63, which sits just inside the Chamber 51, acting as a stop to the fluid traveling within the Chamber 51, channeling the fluid toward the middle of the box;

b) an Entrance Diverter 64, extending down from the top of the Constrictor Frame 63, and extends down into the liquid flow as it is channeled through the Constrictor Frame 63, further forcing the liquid to flow through a gap between the Frame 63 and Entrance Diverter 64;

c) an Inclined Floor 65, uses gravity to keep the flow of liquid through the Chamber 51 and around the agitating elements;

d) Side Diverters 67, which are triangle-shaped in the current embodiment, but could be constructed of other shapes, and mounted to the side walls of the Chamber 51, are placed so the fluid hits the Side Diverters 67, creating turmoil in the flow as it travels between the Side Diverters 67;

e) a Central Diverter 68, which has an irregular triangle shape as shown in FIG. 3, sits directly in the flow of liquid as it travels through the Side Diverters 67;

f) an Angled End Wall 69, which both agitates the fluid further, assisting it to swirl to the Drain 57; where its motion is further obstructed by the g) Drain Separator 73, a thin vertical partition placed directly in the middle of the Drain 57 so that it interrupts the natural swirling that would otherwise occur as fluid circles to leave a tank through a gravity-fed drain, offering one last agitation of the fluid before it departs the Chamber 51.

The inventor has found that these agitating elements encourage the processing fluid to release the gases trapped within it, which leave the Chamber 51 through a Sample Tube 77 set in the top of the Chamber 51, as seen in FIG. 2.

Other shapes may be used to extract more gases, depending on the individual characteristics of the processing fluid and the flow rate; a more viscous fluid moving through the Chamber 51 at a higher rate may allow for a star-shaped Central Diverter 68, for example. The shapes used in the current embodiment have been shown to be suitable for a typical flow rate and viscosity. Similarly, the shape of the Chamber 51 is suitable for mounting above a flow pipe, but other embodiments could be made that are different shapes to allow for more flow, either by making the Chamber 51 wider, or longer with the agitating elements spread farther apart.

The inventor claims:

1. An apparatus used to collect gas samples from a fluid line through which a mixture of liquids and gases flow, comprising:

a. an Agitating Pipe—a pipe installed so that it extends perpendicularly down from the top of a fluid line wall, in which the lower end of the pipe is cut at an angle and length to fit inside the diameter of the fluid line, and the installed pipe is set so that it faces into the fluid flow, and the upper end of the pipe extends up to the exterior of the fluid line;

b. a Gas Trap Expansion Chamber—an enclosed volume in which is fluid from the Agitating Pipe flows through an Entrance Portal into the enclosed volume, through agitating elements which assists to release gas within the fluid before the fluid leaves the volume through a drain; and c. a Sample Tube—set in the top of the Expansion Chamber, taking gases released from the flow liquid from the Expansion Chamber.

2. An apparatus as in claim 1, further comprising a Ball Valve connected between the top end of the Agitating Pipe and Gas Expansion Chamber.

3. An apparatus as in claim 1, in which the Gas Trap Expansion Chamber's agitating elements comprise the following:
a) an Entrance Constrictor Frame, which sits inside the Expansion Chamber, a raised ridge encircling the interior wall of the Chamber such that it acts as a barrier to the fluid flow;
b) an Entrance Diverter, which extends down from the top of the Expansion Chamber and extends down into the liquid flow as it is travels through the Expansion Chamber;
c) an Inclined Floor that uses gravity to compel liquid flow from the Entrance Portal to the Drain;
d) Side Diverters, mounted on the floor of the Expansion Chamber and flush to the walls of the Expansion Chamber, placed to agitate the liquid flow through the Expansion Chamber; and
e) Central Diverters, sitting directly in the flow of liquid in the floor of the Expansion Chamber and away from the Chamber walls, placed to agitate liquid flow through the Expansion Chamber;
f) Angled End Wall, in which one or more Chamber corners near the Drain are angled to assist flow into the Drain; and
g) Drain Separator, a vertical partition placed directly in the Drain that interrupts the natural flow of swirling fluid 5 as it leaves the Chamber through the gravity-fed Drain.

4. An apparatus as in claim 1, in which the Expansion Chamber is a rectangular-prism-shaped box.

5. An apparatus as in claim 3, in which the Expansion Chamber is a rectangular-prism-shaped box and the Expansion Chamber employs all of the agitating elements mentioned.

6. A Gas Trap Expansion Chamber in which liquid-gas mixtures release gases comprising:
a rectangular-prism-shaped box with an Entrance Portal on one wall at one end of the Chamber, a Drain on the opposite end, a Sample Tube set in the top surface of the Expansion Chamber or near the top of one of the Chamber walls from which gas samples can be taken from the Chamber, an Inclined Floor to transport the fluid from the Entrance Portal to the Drain, and a number of agitating elements between the Entrance Portal and the Drain, including:
a) an Entrance Constrictor Frame, which sits inside the Expansion Chamber, a raised ridge encircling the interior wall of the Chamber such that it acts as a barrier to fluid flow;
b) an Entrance Diverter, which extends down from the top of 5 the Expansion Chamber and extends down into the liquid flow as it is travels through the Expansion Chamber;
c) Side Diverters, mounted on the floor of the Expansion Chamber and flush to the walls of the Expansion Chamber; and
e) Central Diverters, sitting directly in the flow of liquid in the floor of the Expansion Chamber and away from the Chamber walls;
f) Angled End Wall, in which one or more Chamber corners near the Drain are angled to assist flow into the Drain; and
g) Drain Separator, a vertical partition placed directly is in the Drain that interrupts the natural flow of swirling fluid as it leaves the Chamber through the gravity-fed Drain.

* * * * *